– – –

United States Patent [19]

Hübner et al.

[11] 4,207,341
[45] Jun. 10, 1980

[54] HYPOGLYCAEMICALLY AND HYPOLIPIDAEMICALLY ACTIVE DERIVATIVES OF PHENYLACETIC ACID

[75] Inventors: Manfred Hübner, Ludwigshafen am Rhein; Hans Kühnle, Mannheim-Neuostheim; Ernst-Christian Witte, Mannheim; Ruth Heerdt, Mannheim-Feudenheim; Rudi Weyer, Frankfurt; Volker Hitzel, Lorsbach, all of Fed. Rep. of Germany

[73] Assignee: Boehringer-Mannheim GmbH, Mannheim, Fed. Rep. of Germany

[21] Appl. No.: 701,717

[22] Filed: Jul. 1, 1976

[30] Foreign Application Priority Data

Jul. 19, 1975 [DE] Fed. Rep. of Germany ....... 2532420

[51] Int. Cl.$^2$ ................. A61K 31/195; C07C 101/42; C07C 101/44
[52] U.S. Cl. ........................... 424/319; 260/326.13 R; 260/346.73; 424/309; 546/291; 546/156; 549/72; 549/73; 560/37; 560/42; 560/45; 560/47; 560/48; 562/433; 562/442; 562/455; 562/456; 562/457
[58] Field of Search ............... 260/471 R; 560/37, 47, 560/48, 42, 45; 562/442, 455, 457, 433, 456; 424/309, 319

[56] References Cited

U.S. PATENT DOCUMENTS

| 3,629,450 | 12/1971 | Greenfeld et al. | 424/319 |
| 4,113,871 | 9/1978 | Stach et al. | 424/272 |

FOREIGN PATENT DOCUMENTS

2500157 7/1976 Fed. Rep. of Germany ............ 560/39

OTHER PUBLICATIONS

McKillop et al., J.A.C.S., 93(19), 4919-4920 (1971).

*Primary Examiner*—Joseph E. Evans
*Assistant Examiner*—G. T. Breitenstein
*Attorney, Agent, or Firm*—Sprung, Felfe, Horn, Lynch & Kramer

[57] ABSTRACT

Phenylacetic acid derivatives of the formula

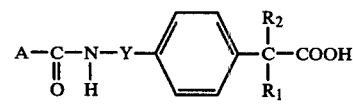

wherein
A is an aryl radical optionally substituted by halogen, trifluoromethyl, alkyl, alkoxy, alkenyloxy, alkoxyalkoxy, alkyl-substituted amino or aryloxy, or a heterocyclic ring system optionally substituted by halogen, alkyl or alkoxy,
Y is a valency bond or an optionally branched alkylene radical containing up to 3 carbon atoms, and
$R_1$ and $R_2$ each independently is hydrogen or a lower alkyl radical, or a physiologically compatible salt or ester thereof, exhibit marked hypoglycaemic and hypolipidaemic activity.

11 Claims, No Drawings

HYPOGLYCAEMICALLY AND HYPOLIPIDAEMICALLY ACTIVE DERIVATIVES OF PHENYLACETIC ACID

The present invention relates to the preparation of hypoglycaemically and hypolipidaemically active phenylacetic acid derivatives.

The phenylacetic acid derivatives according to the present invention are compounds of the general formula

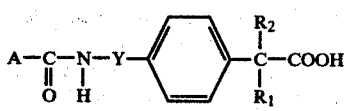 (I)

wherein
A is an aryl radical optionally substituted by halogen, trifluoromethyl, alkyl, alkoxy, alkenyloxy, alkoxyalkoxy, alkyl-substituted amino or aryloxy, or a heterocyclic ring system optionally substituted by halogen, alkyl or alkoxy,
Y is a valency bond or an optionally branched alkylene radical containing up to 3 carbon atoms, and
$R_1$ and $R_2$ each independently is hydrogen or a lower alkyl radical,
or a physiologically compatible salt or ester thereof.

By alkyl and alkenyl, there are to be understood, in all cases, radicals with up to 5 and preferably up to 3 carbon atoms. The alkyl radical is preferably a methyl radical and the alkoxy radical is preferably a methoxy to pentyloxy radical. Alkyl-substituted amino is preferably a dimethylamino radical. The alkenyloxy radical is preferably an allyloxy radical, the aryloxy radical is preferably a phenoxy radical and the alkoxyalkoxy radical is a radical with 2 to 5 carbon atoms and is especially a methoxyethoxy radical. The aryl radical is to be understood to be an aromatic radical containing 6 to 10 carbon atoms and is preferably a naphthyl or phenyl radical.

The optionally substituted heterocyclic ring system is preferably a thienyl, pyridyl, pyrazinyl, chromanyl, quinolyl, indolyl or optionally hydrogenated benzofuranyl radical.

Halogen is to be understood to mean preferably fluorine, chlorine or bromine.

The new compounds of general formula (I) according to the present invention and the physiologically compatible salts and esters thereof possess surprisingly outstanding hypoglycaemic and/or hypolipidaemic effects.

The new compounds according to the present invention can be prepared, for example, by one of the following methods:

(a) reaction of an amine of the general formula

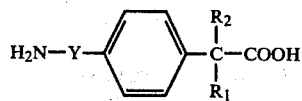 (II)

wherein Y, $R_1$ and $R_2$ have the same meanings as above an acid derivative thereof with a reactive derivative an acid of the general formula A-COOH, wherein A has same meaning as above; or (b) oxidation of a compound of the general formula

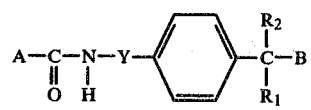 (III)

wherein A, Y, $R_1$ and $R_2$ have the same meanings as above and B is a residue which can be oxidatively converted into a carboxyl group; or (c) reduction of a compound of the general formula

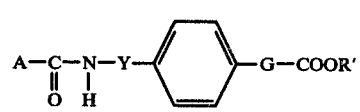 (IV), wherein A and Y have the same meanings as above, R' is a hydrogen atom or an alkyl radical containing up to 4 carbon atoms and G is a

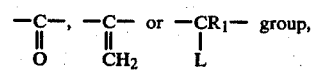 group, in which $R_1$ has the same meaning as above and L is a halogen atom or a hydroxyl group; or (d) for the case in which $R_2$ in general formula (I) represents a hydrogen atom, reaction of a ketone of the general formula:

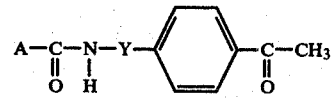 (V), in which A and Y have the same meanings as above, under the conditions of a possibly modified Willgerodt-Kindler synthesis; or (e) for the case in which $R_1$ and $R_2$ in general formula (I) represent hydrogen atoms, reaction of a derivative of a carboxylic acid of the general formula:

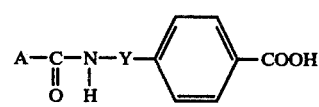 (VI), wherein A and Y have the same meanings as above, with diazomethane according to the Arndt-Eistert method; or (f) reaction of a compound of the general formula:

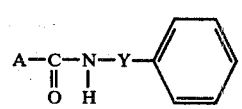 (VII), wherein A and Y have the same meanings as above, under the conditions of a Friedel-Crafts reaction, with a compound of the general formula:

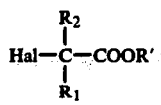 (VIII)

wherein $R_1$, $R_2$ and $R'$ have the same meanings as above and Hal is a halogen atom; or, for the case in which $R_1$ and $R_2$ in general formula (I) each represent a methyl radical, reaction with an acrylic acid derivative of the general formula:

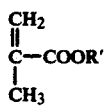 (IX), wherein $R'$ has the same meaning as above; whereafter an acid derivative obtained of general formula (I) is, if desired, converted into the free acid or a free acid obtained of general formula (I) is, if desired, esterified or, if desired, a free acid of general formula (I) is converted into a physiologically compatible acid-addition salt and, when $R_1$ and/or $R_2$ is a hydrogen atom, the product obtained is, if desired, subsequently alkylated.

In the case of process (a), as reactive derivatives of the acid A.COOH, there is preferably used an acid chloride which can be obtained in the usual manner, for example, by reaction of the carboxylic acid with thionyl chloride. However, the esters, azides, anhydrides or mixed anhydrides can be used just as well. The reaction with the compound of general formula (II) can be carried out according to the Schotten-Baumann method. If it is desired to work under anhydrous conditions, then it is preferable to use anhydrous pyridine or some other organic solvent, preferably toluene, acetone or dioxane with an addition of a tertiary amine, for example triethylamine. Instead of the free amino compound, the salts thereof can also be employed.

As acid derivatives of the compounds of general formula (II), there are preferably used the esters, especially the methyl and ethyl esters, nitriles, acid amides and acid anhydrides which then, after the reaction has taken place, can, if necessary, be converted by hydrolysis in known manner into the free carboxylic acids.

The compounds of general formula (II) are new and can be prepared, for example, by hydrolysis of a compound of the general formula:

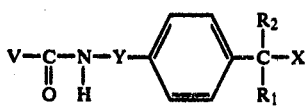 (X)

wherein Y, $R_1$ and $R_2$ have the same meanings as above, V is an aryl, lower alkyl or alkoxy radical and X is a residue which can be converted into a carboxylic acid group by saponification.

Compounds of the general formula (II), in which $R_1$ is a hydrogen atom, can also be obtained by saponifying and decarboxylating a compound of the general formula:

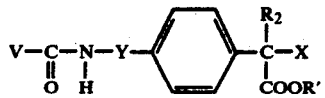 (XI), wherein V, Y, $R_2$, $R'$ and X have the same meanings as above.

The oxidizable group B in compounds of general formula (III) is preferably a hydroxymethyl, aminomethyl or formyl radical and, when $R_1$ and/or $R_2$ is an alkyl radical, can also be an acetyl radical, or a functional derivative thereof, which can easily be oxidized to a carboxyl group with a conventional oxidation agent, for example, a permanganate or dichromate, in the case of the formyl group also with atmospheric oxygen or silver oxide and in the case of the acetyl radical also by means of sodium hypobromite.

The compounds of general formula (III), which are used as starting materials in process (b), are also new. Furthermore, the compounds of general formula (III) in which B is a hydroxymethyl or formyl group also possess hypoglycaemic and/or hypolipidaemic effectiveness. They can be prepared in known manner, especially in a manner analogous to that of process (a), whereby, instead of the acid of the general formula (II), there is used the corresponding compound containing the oxidizable group B. Of course, the other way round, compounds of general formula (I) or the acid derivatives thereof, for example, esters, acid halides and acid amides, can also be reduced to give compounds of general formula (III).

The compounds of general formula (IV), in which G is a —CO— group, employed as starting materials in the case of process (c), can be prepared by the reaction of a compound of general formula (VII) with a compound of the general formula:

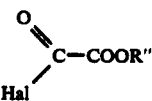 (XII)

wherein Hal has the same meaning as above and $R''$ is a lower alkyl radical, preferably a methyl or ethyl radical, under the conditions of a Friedel-Crafts reaction. The esters thus obtained can be subsequently saponified to the corresponding acids.

The reduction of compounds of general formula (IV), in which G is a —CO— group, can be carried out in the manner of a Clemmensen reduction or by the Wolff-Kishner method with hydrazine/alkali. However, the reduction is preferably carried out catalytically in the presence of noble metals, such as platinum or palladium. In this case, the preferred solvent is glacial acetic acid to which is added a trace of sulfuric or perchloric acid or a molar amount of hydrochloric acid. The reaction temperature is from 20° to 60° C. and the pressure used can be from 1 to 10 ats.

Compounds of the general formula (IV) in which G is a —CH(OH)— group, can be prepared, for example, by reduction of the corresponding keto compounds. The reduction can be carried out catalytically in the presence of noble metals, for example palladium or platinum. Complex metal hydrides can also be used as reducing agents, sodium borohydride preferably being used. In this case, the reaction can be carried out in an alcohol, especially in methanol, or also in an aqueous alkaline medium. The halogen derivatives can also be prepared from the hydroxy compounds in known manner. The reduction of these halogen derivatives to give compounds of general formula (I) can also be carried out in known manner, for example, with nascent or catalytically activated hydrogen.

Compounds of general formula (IV), in which G is a

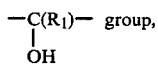

can be prepared by the isonitrile method (cf. Chem. Abs. 68, 68721v/1968), for example from an aryl alkyl ketone; if G is a

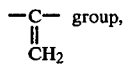

then these compounds can be obtained from compounds of general formula (IV), in which G is a

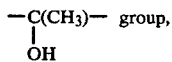

by dehydration.

The acetophenone derivatives of general formula (V) used in process (d) can easily be obtained by acetylation by the Friedel-Crafts method. For the preparation of compounds of general formula (I), in which $R_1$ and $R_2$ each represent hydrogen atoms, compounds of general formula (V) are reacted, according to the Willgerodt-Kindler synthesis, with sulfur and a secondary amine, preferably morpholine. The thiomorpholide obtained in the case of the Willgerodt-Kindler synthesis is saponified in known manner to give a carboxylic acid of general formula (I).

Instead of sulfur and the secondary amine, for the simultaneous reduction of the carbonyl group to a methylene radical and oxidation of the methyl radical to a carboxyl radical, there can also be used thallic salts, preferably thallic nitrate, and perchloric acid.

For the case in which compounds of general formula (I) are to be prepared in which $R_1$ is a methyl radical and $R_2$ is a hydrogen atom, the ketone of general formula (V) can be first condensed with rhodanine. It is subsequently saponified and the α-thiopyruvic acid obtained converted, under the conditions of a Willgerodt-Kindler synthesis, into the thiomorpholide, which is subsequently saponified to give a carboxylic acid.

Process (e) incorporates the Arndt-Eistert method in which a derivative, especially a chloride, of a carboxylic acid of general formula (VI) is converted by means of diazomethane into a diazoketone. By means of the action of ultra-violet light, heat or catalysts, for example, silver oxide, the diazoketone is converted into a phenyl acetic acid of general formula (I).

If compounds of general formula (I) are to be synthesized according to process (f), then compounds of general formula (VII) are condensed in the presence of aluminum chloride with a substituted haloacetic acid ester or with a methacrylic acid derivative in an appropriate solvent, for example ethylene chloride, at a reaction temperature of from 0° to 80° C.

When it is desired to carry out esterification of carboxylic acids of general formula (I), there can, in principle, be used all alcohols. The preferred alcohols include alkanols containing up to 5 carbon atoms as well as amino, alkylamino, hydroxy and alkoxy substitution products thereof containing up to about 5 carbon atoms in the substituent, e.g. the lower monohydroxy alcohols, for example, methanol, ethanol or n-propanol, as well as polyhydroxy alcohols, for example glycol, or alcohols containing other functional groups, for example ethanolamine or glycol ethers.

When it is desired to carry out a subsequent alkylation of compounds of general formula (I), in which $R_1$ and/or $R_2$ each represent hydrogen atoms, then this can be carried out in the usual manner with conventional alkylation agents, for example alkyl halides or dialkyl sulfates.

The physiologically compatible salts are, in particular, the alkali metal, alkaline earth metal and ammonium salts, as well as salts with blood sugar-lowering basic compounds, preferably biguanides. The preparation of these salts is carried out in the usual way, for example, by reaction with the corresponding free bases or carbonates.

As blood sugar-lowering and/or anti-hyperlipidaemic compositions according to the present invention, there can be considered all the conventional oral and parenteral forms of administration, for example, tablets, capsules, dragees, syrups, solutions, suspensions, drops, suppositories and the like. For this purpose, the active material is mixed with solid or liquid carrier materials and subsequently brought into the desired form. Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents. As injection medium, it is preferred to use water which contains the conventional additives for injection solutions, such as stabilizing agents, solubilizing agents and/or buffers. Additives of this type include, for example, acetate and tartrate buffers, ethanol, complex-forming agents (such as ethylenediamine-tetraacetic acid and the nontoxic salts thereof) and high molecular weight polymers (such as polyethylene oxide) for viscosity regulation.

The following Examples are given for the purpose of illustrating the present invention:

EXAMPLE 1

4-(5-Chloro-2-methoxybenzamido)-phenylacetic acid 8.9 g Ethyl 4-aminophenylacetate are suspended in 200 ml. toluene. After the addition of 4 ml pyridine, a solution of 10.2 g 5-chloro-2-methoxybenzoyl chloride in 10 ml toluene is added dropwise thereto and the reaction mixture heated under reflux for 2 hours. After cooling, the toluene phase is successively shaken out with dilute hydrochloric acid, aqueous sodium bicarbonate solution and water and thereafter dried and evaporated. The evaporation residue is then recrystallized twice from ethanol to give 12.2 g (70% of theory)

ethyl 4-(5-chloro-2-methoxybenzamido)-phenylacetate; m.p. 104° C.

5.2 g of this ethyl ester are heated for 2 hours on a steambath in 80 ml 1 N aqueous sodium hydroxide solution. The solution thus obtained is filtered with charcoal, acidified with hydrochloric acid and the precipitated 4-(5-chloro-2-methoxybenzamido)-phenylacetic acid is filtered off and recrystallized from ethanol. The yield is 2.8 g (58% of theory); m.p. 199°-201° C.

In an analogous manner, there are obtained, by reaction of ethyl 4-aminophenylacetate
(a) with 2-ethoxy-5-chlorobenzoyl chloride, ethyl 4-(2-ethoxy-5-chlorobenzamido)-phenylacetate; m.p. 121°-122° C., after recrystallization from ethanol; and from this, by saponification, 4-(2-ethoxy-5-chlorobenzamido)-phenyl-acetic acid; m.p. 199°-200° C., after recrystallization from ethanol;
(b) with 2-methoxy-5-methylbenzoyl chloride, ethyl 4-(2-methoxy-5-methylbenzamido)-phenylacetate; m.p. 69°-70° C., after recrystallization from ethanol; and from this, by saponification, 4-(2-methoxy-5-methylbenzamido)-phenylacetic acid; m.p. 140°-142° C., after recrystallization from ethanol;
(c) with 2-pentyloxy-5-chlorobenzoyl chloride, ethyl 4-(2-pentyloxy-5-chlorobenzamido)-phenylacetate, m.p. 69°-71° C. (crude melting point); and from this, by saponification, 4-(2-pentyloxy-5-chlorobenzamido)-phenylacetic acid; m.p. 144° C., after recrystallization from ethanol;
(d) with 2-butyloxy-5-chlorobenzoyl chloride, ethyl 4-(2-butyloxy-5-chlorobenzamido)-phenylacetate; m.p. 77°-80° C. (crude melting point); and from this, by saponification, 4-(2-butyloxy-5-chlorobenzamido)-phenylacetic acid; m.p. 158° C., after recrystallization from ethanol;
(e) with 3,5-dichlorobenzoyl chloride, ethyl 4-(3,5-dichlorobenzamido)-phenylacetate; m.p. 152° C. (crude melting point); and from this, by saponification, 4-(3,5-dichlorobenzamido)-phenylacetic acid; m.p. 189° C., after recrystallization from ethanol-water.

EXAMPLE 2

4-(4-Chlorobenzamido)-phenylacetic acid 7.6 g 4-Aminophenylacetic acid are dissolved in 50 ml 2 N aqueous sodium hydroxide solution and 50 ml acetone. A solution of 8.8 g 4-chlorobenzoyl chloride in 10 ml acetone is added dropwise thereto at 0° C. The reaction mixture is further stirred for 3 hours at ambient temperature, then diluted with water, filtered and the filtrate acidified with dilute hydrochloric acid. The precipitate obtained is reprecipitated via its sodium salt and recrystallized from ethanol. There are obtained 4.2 g (29% of theory) 4-(4-chlorobenzamido)-phenylacetic acid; m.p. 252° C.

EXAMPLE 3

4-(5-Chloro-2-methoxybenzamidomethyl)-phenylacetic acid

A solution of 5.0 g 5-chloro-2-methoxybenzoyl chloride in 10 ml acetone is added, with ice cooling, to a solution of 5.0 g 4-aminomethyl-phenylacetic acid hydrochloride in 25 ml 2 N aqueous sodium hydroxide solution and 25 ml acetone. The reaction mixture is then stirred for 3 hours at ambient temperature, diluted with water, filtered with charcoal and the filtrate acidified with 2 N hydrochloric acid. The precipitate obtained is filtered off with suction and dried and then recrystallized from ethyl acetate/petroleum ether. There is obtained 1.8 g (21% of theory) 4-(5-chloro-2-methoxybenzamidomethyl)-phenylacetic acid; m.p. 140°-141° C.

The 4-aminomethylphenylacetic acid hydrochloride (m.p. 220° C.) used as starting material is obtained by the catalytic hydrogenation of ethyl 4-cyanophenylacetate and subsequent saponification with hydrochloric acid.

In an analogous manner, from 4-aminomethylphenylacetic acid hydrochloride and 2-ethoxy-5-chlorobenzoyl chloride, there is obtained 4-(2-ethoxy-5-chlorobenzamidomethyl)-phenylacetic acid; m.p. 175° C., after recrystallization from ethanol.

EXAMPLE 4

4-(2-Butoxy-5-chlorobenzamidomethyl)-phenylacetic acid 11.5 g Ethyl 4-aminomethylphenylacetate hydrochloride (m.p. 172° C.; prepared by the catalytic hydrogenation of ethyl 4-cyanophenylacetate) are suspended in 200 ml toluene. After the addition of 13.9 ml triethylamine, there is added dropwise, while cooling, a solution of 12.4 g 2-butoxy-5-chlorobenzoyl chloride in 10 ml toluene. The reaction mixture is subsequently heated under reflux for 2 hours, while stirring. After cooling, the toluene phase is treated successively with dilute hydrochloric acid, aqueous sodium bicarbonate solution and water and then evaporated. The evaporation residue is heated on a steambath with 2 N aqueous sodium hydroxide solution and the solution then filtered. The filtrate is acidified with dilute hydrochloric acid. The precipitated 4-(2-butoxy-5-chlorobenzamidomethyl)-phenylacetic acid is reprecipitated via its sodium salt and recrystallized from ethanol. The yield is 3.9 g (20% of theory); m.p. 198° C.

EXAMPLE 5

4-(2-Benzamidoethyl)-phenylacetic acid 9.6 g 4-(2-Benzamidoethyl)-acetophenone, well mixed with 1.8 g sulfur are suspended in 15 g morpholine and heated under reflux for 18 hours. After cooling, the reaction mixture is dissolved in 50 ml ethanol and filtered. The filtrate is evaporated and the residue well washed with water and diethyl ether. The resultant 4-(2-benzamidoethyl)-phenylthioacetomorpholide is recrystallized from diethyl ether. The yield is 7.1 g (54% of theory); m.p. 130°-132° C.

3.4 g of the thiomorpholide of the substituted phenylacetic acid are boiled for 9 hours in 25 ml ethanol with 1 g potassium hydroxide. The reaction mixture is then evaporated and the residue stirred with water. The precipitated 4-(2-benzamidoethyl)-phenylacetic acid morpholide is then filtered off with suction. The yield is 2.8 g (85% of theory); m.p. 122°-123° C.

After boiling 2.8 g of the morpholide for 50 hours with 0.8 g sodium hydroxide and 20 ml ethanol, there is obtained 1.2 g (53% of theory) 4-(2-benzamidoethyl)-phenylacetic acid; m.p. 157°-158° C.

EXAMPLE 6

4-[2-(2-Butoxy-5-chlorobenzamido)-ethyl]-phenylacetic acid

To a solution of 12.2 g. ethyl 4-(2-aminoethyl)-phenylacetate hydrochloride in 40 ml dioxane and 40 ml acetone, there is added dropwise, after the addition of 8 ml pyridine, a solution of 12.3 g 2-butoxy-5-chlorobenzoyl chloride in 10 ml acetone. The reaction mixture is then stirred under reflux for 3 hours and thereafter evaporated in a vacuum. The residue is stirred with dilute hydrochloric acid and then with aqueous sodium bicarbonate solution, filtered with suction and washed with water. There are obtained 19 g of crude product which, after recrystallization from ethanol, with the addition of small amounts of water, gives ethyl 4-[2-(2-butoxy-5-chlorobenzamido)-ethyl]-phenylacetate; m.p. 80° C.

9.0 g of the crude ethyl ester are heated with 2 N aqueous sodium hydroxide solution, after the addition of a little ethanol, on a steambath until solution is complete. After distilling off the alcohol, the reaction mixture is filtered with charcoal and the filtrate is filtered with charcoal and the filtrate is acidified with 2 N hydrochloric acid. The precipitate obtained is, after drying, recrystallized from ethyl acetate. There are obtained 4.0 g. (47% of theory) 4-[2-(2-butoxy-5-chlorobenzamido)-ethyl]-phenylacetic acid; m.p. 131°–132° C.

The ethyl 4-(2-aminoethyl)-phenylacetate hydrochloride used as starting material is prepared in the following manner: 4-(2-acetamidoethyl)-acetophenone is reacted with morpholine and sulfur to give the thiomorpholide of 4-(2-acetamidoethyl)-phenylacetic acid (m.p. 117°–118° C.). Subsequent alkaline saponification, followed by esterification with ethanolic hydrochloric acid, gives ethyl 4-(2-aminoethyl)-phenylacetate hydrochloride; m.p. 177°–178° C., after recrystallization from ethanol.

In an analogous manner, there are obtained, by the reaction of ethyl 4-(2-aminoethyl)-phenylacetate hydrochloride:

(a) with 5-chloro-2-methoxybenzoyl chloride, via ethyl 4-[2-(5-chloro-2-methoxybenzamido)-ethyl]-phenylacetate (oil), 4-[2-(5-chloro-2-methoxybenzamido)-ethyl]-phenylacetic acid; m.p. 127° C., after recrystallization from ethyl acetate;

(b) with 2-ethoxy-5-chlorobenzoyl chloride, via ethyl 4-[2-(2-ethoxy-5-chlorobenzamido)-ethyl]-phenylacetate (oil), 4-[2-ethoxy-5-chlorobenzamido)-ethyl]-phenylacetic acid; m.p. 137°–138° C., after recrystallization from ethanol-water and ethyl acetate-petroleum ether;

(c) with 2-allyloxy-5-chlorobenzoyl chloride, via ethyl 4-[2-(2-allyloxy-5-chlorobenzamido)-ethyl]-phenylacetate, 4-[2-(2-allyloxy-5-chlorobenzamido)-ethyl]-phenylacetic acid; m.p. 104°–105° C., after recrystallization from ethyl acetate.

EXAMPLE 7

4-[2-(2-Methoxy-5-methylbenzamido)-ethyl]-phenylacetic acid 3.4 g 2-Methoxy-5-methylbenzoic acid are heated under reflux with 6 ml thionyl chloride for 2 hours. The reaction mixture is then evaporated and the residue taken up in 15 ml methylene chloride. The solution is added dropwise to a suspension of 4.8 g ethyl 4-(2-aminoethyl)-phenylacetate hydrochloride in 20 ml 2 N aqueous sodium hydroxide solution, while cooling with ice. By the addition of further aqueous sodium hydroxide solution, the pH value of the solution is maintained at 12. The reaction mixture is then stirred for 1 hour at ambient temperature, whereafter the methylene chloride phase is separated off and shaken out three times with 1 N aqueous sodium hydroxide solution, dried and evaporated. There are obtained 3.6 g (51% of theory) ethyl 4-[2-(2-methoxy-5-methylbenzamido)-ethyl]-phenylacetate in the form of an oil which is not further purified for the subsequent reaction.

3.6 g of this ethyl 4-[2-(2-methoxy-5-methylbenzamido)-ethyl]-phenylacetate are dissolved in 30 ml ethanol, 0.8 g sodium hydroxide is added thereto and the reaction mixture is boiled under reflux for 3 hours. It is then evaporated, the residue is dissolved in water and, after the addition of active charcoal, is filtered. By the addition of 2 N hydrochloric acid, the 4-[2-(2-methoxy-5-methylbenzamido)-ethyl]-phenylacetic acid is precipitated out. After drying, it is recrystallized from benzene. The yield is 1.8 g. (55% of theory); m.p. 83°–85° C., after recrystallization from benzene.

In an analogous manner, there are obtained, by the reaction of ethyl 4-(2-aminoethyl)-phenylacetate hydrochloride (a) with 5-chloro-2-methyl-2,3-dihydrobenzo[b]furoyl chloride, via ethyl 4-[2-(5-chloro-2-methyl-2,3-dihydrobenzo[b]furoyl-(7)-amino)-ethyl]-phenylacetate (oil); 4-[2-(5-chloro-2-methyl-2,3-dihydrobenzo[b]furoyl-(7)-amino)-ethyl]-phenylacetic acid; m.p. 145°–148° C., after recrystallization from isopropanol;

(b) with 5-chloro-2-phenoxybenzoyl chloride, via ethyl 4-[2-(5-chloro-2-phenoxybenzamido)-ethyl]-phenylacetate (oil), 4-[2-(5-chloro-2-phenoxybenzamido)-ethyl]-phenylacetic acid; m.p. 132°–135° C., after recrystallization from isopropanol;

(c) with 5-bromo-2-methoxybenzoyl chloride, via ethyl 4-[2-(5-bromo-2-methoxybenzamido)-ethyl]-phenylacetate (oil), 4-[2-(5-bromo-2-methoxybenzamido)-ethyl]-phenylacetic acid; m.p. 148°–150° C., after recrystallization from isopropanol.

EXAMPLE 8

4-[2-(4-Chlorobenzamido)-ethyl]-phenylacetic acid 8.3 g 4-Chlorobenzoyl chloride are added dropwise at 5°–10° C., within the course of 10 minutes, to a solution of 11.0 g ethyl 4-(2-aminoethyl)-phenylacetate in 90 ml anhydrous pyridine. The reaction mixture is then stirred for 90 minutes at 10° C., subsequently allowed to warm up to 20° C. and thereafter warmed to 40°–45° C. for 30 minutes. The reaction mixture is then cooled and stirred into 900 ml ice water, a solid precipitate thereby being obtained. This is filtered off with suction and washed with water. There are obtained 14.5 g (94% of theory) of crude product which is recrystallized from isopropanol to give 10.9 g (70% of theory) ethyl 4-[2-(4-chlorobenzamido)-ethyl]-phenylacetate; m.p. 118°–119° C.

13.5 g ethyl 4-[2-(4-chlorobenzamido)-ethyl]-phenylacetate, dissolved in 110 ml methanol and 39 ml 2 N aqueous potassium hydroxide solution, are maintained at reflux temperature for 12 hours. The solution is then evaporated in a vacuum. After dilution with water, it is extracted with diethyl ether, the aqueous phase is filtered, with the addition of active charcoal, and the filtrate is acidified. There are obtained 11.7 g (95% of theory) of acid which is recrystallized from 25 ml glacial acetic acid. There are obtained 8.2 g (66% of theory) 4-[2-(4-chlorobenzamido)-ethyl]-phenylacetic acid; m.p. 186°–187° C. From the mother liquor, there is obtained a further 1.9 g (15% of theory) of this acid, which has a melting point of 182°–183° C.

In an analogous manner, by the reaction of ethyl 4-(2-aminoethyl)-phenylacetate with 5-chloro-2-methoxybenzoyl chloride, there is obtained, via ethyl 4-[2-(5-chloro-2-methoxybenzamido)-ethyl]-phenylacetate (oil), 4-[2-(5-chloro-2-methoxybenzamido)-ethyl]-phenylacetic acid; m.p. 127°–128° C., after recrystallization from 75% acetic acid.

EXAMPLE 9

4-[2-(2-Methoxynicotinoylamino)-ethyl]-phenylacetic acid 7.65 g 2-methoxynicotinic acid are suspended in 200 ml tetrahydrofuran, and, after the addition of 22 ml triethylamine, cooled to 0° C. 4.8 ml methyl chloroformate are added thereto dropwise at 0° C., while stirring, and stirring is thereafter continued at 0° C. for 30 minutes. 12.2 g ethyl 4-(2-aminoethyl)-phenylacetate hydrochloride are now added portionwise and the reaction mixture thereafter stirred for 1 hour at 0° C. and for 3 hours at ambient temperature. The reaction mixture is then evaporated in a vacuum and 200 ml water added thereto. The ester, which separates out as an oil, is taken up in ethyl acetate, the ethyl acetate phase is shaken out successively with dilute acetic acid, aqueous sodium bicarbonate solution and water and, after drying, is evaporated. The residue is heated on a steambath in 20 ml 2 N aqueous sodium hydroxide solution and 50 ml ethanol for 4 hours. After distilling off the ethanol, the solution is filtered and acidified with 2 N acetic acid. The precipitated 4-[2-(2-methoxynicotinoylamino)-ethyl]-phenylacetic acid is filtered off with suction and recrystallized from ethanol; the yield is 5.4 g (34% of theory); m.p. 159°–160° C.

In an analogous manner, there is obtained, by the reaction of ethyl 4-(2-aminoethyl)-phenylacetate hydrochloride:

(a) with 6-chloroquinoline-8-carboxylic acid, via ethyl 4-[2-(6-chloroquinoline-8-carboxamido)-ethyl]-phenylacetate (oil), 4-[2-(6-chloroquinoline-8-carboxamido)-ethyl]-phenylacetic acid; m.p. 185°–187° C., after recrystallization from ethanol;

(b) with 5-chloro-3-methoxythiophene-2-carboxylic acid, via ethyl 4-[2-(5-chloro-3-methoxythenoyl-(2)-amino)-ethyl]-phenylacetate (oil), 4-[2-(5-chloro-3-methoxythenoyl-(2)-amino)-ethyl]-phenylacetic acid; m.p. 141° C., after recrystallization from ethyl acetate;

(c) with 5-bromo-2-methoxynicotinic acid, via ethyl 4-[2-(5-bromo-2-methoxynicotinoylamino)-ethyl]-phenylacetate (oil), 4-[2-(5-bromo-2-methoxynicotinoylamino)-ethyl]-phenylacetic acid; m.p. 160°–162° C., after recrystallization from ethanol;

(d) with 6-chlorochromane-8-carboxylic acid, via ethyl 4-[2-(6-chlorochromane-8-carboxamido)-ethyl]-phenylacetate (oil), 4-[2-(6-chlorochromane-8-carboxamido)-ethyl]-phenylacetic acid; m.p. 171°–173° C., after recrystallization from ethanol;

(e) with 5-chloro-2-methoxynicotinic acid, via ethyl 4-[2-(5-chloro-2-methoxynicotinoylamino)-ethyl]-phenylacetate (oil), 4-[2-(5-chloro-2-methoxynicotinoylamino)-ethyl]-phenylacetic acid; m.p. 157°–158° C., after recrystallization from ethanol.

EXAMPLE 10

4-[2-(5-Chloro-2-methoxybenzamido)-ethyl]-phenylacetic acid 3.3 g 4-[2-(5-chloro-2-methoxybenzamido)-ethyl]-acetophenone (m.p. 100°–101° C.; prepared by the reaction of 5-chloro-2-methoxybenzoyl chloride with 4-(2-aminoethyl)-acetophenone hydrochloride), are suspended in 25 ml methanol. After the addition of 5 ml 70% perchloric acid, 3.9 g thallic nitrate trihydrate are added thereto, while stirring. After a short time, the thallous nitrate formed precipitates out. The reaction mixture is left to stand for 3 days, then filtered with suction and the filtrate is diluted with water and extracted with chloroform. After drying the chloroform extract over anhydrous sodium acetate, it is filtered and the filtrate evaporated. The residue obtained is treated with 2 N aqueous sodium hydroxide solution. After filtering and acidifying, 4-[2-(5-chloro-2-methoxybenzamido)-ethyl]-phenylacetic acid precipitates out. It is filtered off and recrystallized twice from ethyl acetate. The yield is 0.5 g (15% of theory); m.p. 125°–126° C.

EXAMPLE 11

2-{4-[2-(5-Chloro-2-methoxybenzamido)-ethyl]-phenyl}-propionic acid 2.5 g 5-Chloro-2-methoxybenzoyl chloride, dissolved in 20 ml methylene chloride, is slowly added, while stirring, to a solution of 3 g ethyl 2-[4-(2-aminoethyl)-phenyl]-propionate hydrochloride in 12 ml 1 N aqueous sodium hydroxide solution. The solution is maintained at pH 10 by the addition of aqueous sodium hydroxide solution. The reaction mixture is further stirred for 2 hours, the organic phase is then separated off, shaken out twice with 2 N aqueous sodium hydroxide solution and once with 2 N hydrochloric acid and then evaporated. 4 g of the oily residue obtained are boiled for 2 hours with 14 ml 2 N aqueous sodium hydroxide solution for the saponification of the ester group. After cooling, the solution is acidified, the desired 2-{4-[2-(5-chloro-2-methoxybenzamido)-ethyl]-phenyl}-propionic acid thereby precipitating out. For purification, the product is first dissolved in an aqueous solution of sodium carbonate, again precipitated out by the addition of hydrochloric acid and subsequently recrystallized from isopropanol. The yield is 1.9 g (47% of theory); m.p. 143°–144° C.

For the preparation of the ethyl 2-[4-(2-aminoethyl)-phenyl]-propionate used as starting material, ethyl 2-phenylpropionate is chloromethylated, the ethyl 2-(p-chloromethylphenyl)-propionate (b.p. 120°–122° C./0.3 mm Hg) thus obtained is reacted with sodium cyanide to give ethyl 2-(4-cyanomethylphenyl)-propionate (b.p. 149°–150° C./0.4 mm Hg) and, by the catalytic hydrogenation of the nitrile group in the presence of a palladium/charcoal catalyst in hydrochloric alcoholic solution, there is obtained the hydrochloride of ethyl 2-[4-(2-aminoethyl)-phenyl]-propionate; m.p. 124°–125° C.

EXAMPLE 12

4-[2-(2-Methoxybenzamido)-ethyl]-phenylacetic acid 5.5 g 4-[2-(5-Chloro-2-methoxybenzamido)-ethyl]-phenylglyoxylic acid are hydrogenated in 100 ml glacial acetic acid/0.5 ml perchloric acid in the presence of 0.5 g palladium/charcoal at 40° C. After completion of the take up of hydrogen, the reaction mixture is filtered, the filtrate is concentrated to one half of its original volume, 10 ml concentrated hydrochloric acid are added thereto and the solution then extracted several times with methylene chloride. The organic phase is dried and evaporated. The residue is dissolved in 2 N aqueous sodium hydroxide solution, active charcoal is added thereto, followed by suction filtration and the filtrate is mixed with concentrated hydrochloric acid. An oil separates out. After dissolving this oil in hot isopropanol and adding water, the desired 4-[2-(2-methoxybenzamido)-ethyl]-phenylacetic acid crystallizes out; yield 3.91 g (80% of theory); m.p. 112°–113° C.

For the preparation of the 4-[2-(5-chloro-2-methoxybenzamido)-ethyl]-phenylglyoxylic acid used as starting material, 10 g 4-[2-(5-chloro-2-methoxybenzamido)-ethyl]-acetophenone (cf. Example 10) are suspended in 100 ml water and heated to 70° C. A solution of 16 g potassium permanganate and 6 g potassium hydroxide in 100 ml water, heated to 70° C., is added thereto in 3 portions. After further stirring the reaction mixture for 30 minutes at 70° C., it is filtered with suction while still hot and then acidified. The precipitate obtained is filtered off and recrystallized from isopropanol. There are obtained 5.5 g (49% of theory) of the desired phenylglyoxylic acid derivative; m.p. 154°–155° C.

EXAMPLE 13

2-{4-[2-(4-Chlorobenzamido)-ethyl]-phenyl}-2-methylpropionic acid 9.6 g. 4-Chlorobenzoyl chloride are added dropwise to a solution of 14.1 g ethyl 2-[4-(2-aminoethyl)-phenyl]-2-methylpropionate hydrochloride in 90 ml anhydrous pyridine at 5°–10° C. The reaction mixture is kept at 10° C. for 90 minutes, then allowed to warm up to ambient temperature and subsequently heated to 45° C. for 10 minutes. A part thereof remains undissolved. The reaction mixture is stirred into 750 ml. ice water, filtered with suction and the filter cake then washed. There are obtained 13.2 g (68% of theory) ethyl 2-{4-[2-(4-chlorobenzamido)-ethyl]-phenyl}-2-methylpropionate which, after recrystallization from isopropanol, melts at 108°–109° C.

13.9 g ethyl 2-{4-[2-(4-chlorobenzamido)-ethyl]-phenyl}-2-methylpropionate 100 ml methanol and 37 ml 2 N aqueous potassium hydroxide solution are maintained at reflux temperature for 9 hours, the methanol is then distilled off in a vacuum and the residue is diluted with water and extracted with diethyl ether. The aqueous phase is filtered and acidified. There are obtained 12.8 g (100% of theory) of crude product. After recrystallization from 130 ml glacial acetic acid, there are obtained 12.4 g (94% of theory) 2-{4-[2-(4-chlorobenzamido)-ethyl]-phenyl}-2-methylpropionic acid; m.p. 234°–235° C.

The ethyl 2-[4-(2-aminoethyl)-phenyl]-2-methylpropionate hydrochloride (m.p. 150°–154° C.) used as starting material is obtained by the reaction of 2-(4-chloromethylphenyl)-2-methylpropionic acid (m.p. 121°–122° C.) with sodium cyanide. The 2-(4-cyanomethylphenyl)-2-methylpropionic acid obtained melts at 105°–106° C. This propionic acid derivative is catalytically hydrogenated in ethanolic hydrochloric acid solution to give 2-[4-(2-aminoethyl)-phenyl]-2-methylpropionic acid hydrochloride which, after recrystallization from isopropanol, melts at 247°–248° C. By esterification thereof with ethanol in hydrochloric acid solution, there is obtained the desired ethyl 2-[4-(2-aminoethyl)-phenyl]-2-methylpropionate hydrochloride.

In an analogous manner, by the reaction of ethyl 2-[4-(2-aminoethyl)-phenyl]-2-methylpropionate hydrochloride with 5-chloro-2-methoxybenzoyl chloride, there is obtained, via ethyl 2-{4-[2-(5-chloro-2-methoxybenzamido)-ethyl]-phenyl}-2-methylpropionate (oil), 2-{4-[2-(5-chloro-2-methoxybenzamido)-ethyl]-phenyl}-2-methylpropionic acid; m.p. 149°–150° C., after recrystallization from glacial acetic acid.

EXAMPLE 14

4-[2-(5-Chloro-2-methoxybenzamido)-ethyl]-phenylacetic acid 4.0 g Sodium dichromate dihydrate are added to a solution of 3.3 g 2-{4-[2-(5-chloro-2-methoxybenzamido)-ethyl]-phenyl}-ethanol in 50 ml glacial acetic acid and the reaction mixture is stirred for 3 days at ambient temperature. The glacial acetic acid is distilled off with a rotary evaporator, the residue is taken up with water and dilute aqueous sodium hydroxide solution, a small amount of unreacted starting material is removed by extraction with diethyl ether and, by acidification with hydrochloric acid, 4-[2-(5-chloro-2-methoxybenzamido)-ethyl]-phenylacetic acid is precipitated out. It is filtered off, dried and recrystallized from ethyl acetate; yield 1.8 g (52% of theory); m.p. 124°–126° C.

The 2-{4-[2-(5-chloro-2-methoxybenzamido)-ethyl]-phenyl}-ethanol (oil) used as starting material is obtained by the acylation of 2-[4-(2-aminoethyl)-phenyl]-ethanol (oil) with 5-chloro-2-methoxybenzoyl chloride in anhydrous methylene chloride in the presence of triethylamine as acid acceptor.

EXAMPLE 15

2-{4-[2-(Quinoline-8-carboxamido)-ethyl]-phenyl}-propionic acid 6.0 g Quinoline-8-carbonyl chloride (m.p. 156°–160° C.) are added to 6.0 g ethyl 2-[4-(2-aminoethyl)-phenyl]-propionate hydrochloride in 50 ml methylene chloride and a solution of 7 ml triethylamine in 20 ml methylene chloride slowly added dropwise at 0° C. The reaction mixture is thereafter stirred for 2 hours at ambient temperature, subsequently shaken out 6 times with 2 N aqueous sodium hydroxide solution and twice with 2 N hydrochloric acid, and the methylene chloride phase is then dried and evaporated. The residue is taken up with diethyl ether, undissolved material is filtered off and the diethyl ether is evaporated. Ethyl 2-{4-[2-(quinoline-8-carboxamido)-ethyl]-phenyl}-propionate (oil) remains behind in a yield of 8.0 g (91% of theory). This ester is saponified with 2.0 g sodium hydroxide in 50 ml 80% ethanol by heating under reflux for 2 hours. The reaction mixture is thereafter evaporated to dryness, the residue is taken up in water and diethyl ether, the layers are separated and the aqueous layer acidified. The 2-{4-[2-(quinoline-8-carboxamido)-ethyl]-phenyl}-propionic acid obtained is again reprecipitated by dissolving in dilute aqueous sodium bicarbonate solution and acidifying with hydrochloric acid, whereafter it is recrystallized from 50% isopropanol and then from toluene. The yield is 2.3 g (31% of theory); m.p. 143°–144° C.

In an analogous manner, by the reaction of ethyl 4-(2-aminopropyl)-phenylacetate with o-butoxybenzoyl chloride, there is obtained, via ethyl 4-[2-(2-butoxybenzamido)-propyl]-phenylacetate (oil), 4-[2-(2-butoxybenzamido)-propyl]-phenylacetic acid; m.p. 91°–92° C., after recrystallization from isopropanol/water.

The preparation of the ethyl 4-(2-aminopropyl)-phenylacetate used as starting material is carried out in the following manner: 4-(2-acetamidopropyl)-acetophenone (m.p. 99°–100° C.) is reacted with morpholine and sulfur to give the thiomorpholide of 4-(2-acetamidopropyl)-phenyl-acid acid (m.p. 147° C.). By boiling with 6 N hydrochloric acid, there is obtained 4-(2-aminopropyl)-phenylacetic acid (oily), which is esterified with hydrogen chloride and ethanol. By treating the initially formed hydrochloride with dilute aqueous sodium hydroxide solution, there is obtained the free amino compound in the form of an oil.

EXAMPLE 16

4-[2-(2-Methylquinoline-8-carboxamido)-ethyl]-phenylacetic acid hydrochloride To 6.5 g 2-methylquinoline-8-carboxylic acid and 8.05 g ethyl 4-(2-aminoethyl)-phenylacetate hydrochloric in 120 ml anhydrous methylene chloride are added at −15° C. first 3.3 ml phosphorous oxychloride and then 14.1 ml triethylamine. The reaction mixture is stirred for 1 hour at −15° C. and for 2 hours at ambient temperature, then extracted twice with 50 ml amounts of 1 N hydrochloric acid, deacidified with aqueous sodium bicarbonate solution and the organic phase completely evaporated. There are obtained 5.4 g of the ethyl ester in the form of an oil which is subsequently saponified for 45 minutes on a water bath with a mixture of 25 ml ethanol and 25 ml 2 N aqueous sodium hydroxide solution. The solution is partially evaporated in a rotary evaporator, mixed with water, extracted a few times with methylene chloride and the aqueous phase is treated with active charcoal and, after the addition of a little isopropanol, acidified with concentrated hydrochloric acid to a pH of 1. The solution is cooled and the precipitate is filtered off with suction. There are obtained 4.2 g (31% of theory) 4-[2-(2-methylquinoline-8-carboxamido)-ethyl]-phenylacetic acid hydrochloride; m.p. 232°–235° C.

EXAMPLE 17

In a manner analogous to that described in Example 7, there are obtained, by the reaction of ethyl 4-(2-aminoethyl)-phenylacetate hydrochloride (a) with 5-fluoro-2-methoxybenzoyl chloride, via ethyl 4-[2-(5-fluoro-2-methoxybenzamido)-ethyl]-phenylacetate (oil), 4-[2-(5-fluoro-2-methoxybenzamido)-ethyl]-phenylacetic acid; m.p. 83°–84° C. as the monohydrate, after recrystallization from ethanol/water;

(b) with 3-trifluoromethylbenzoyl chloride, via ethyl 4-[2-(3-trifluoromethylbenzamido)-ethyl]-phenylacetate (oil), 4-[2-(3-trifluoromethylbenzamido)-ethyl]-phenylacetic acid; m.p. 137°–139° C., after recrytallization from ethyl acetate;

(c) with 5-chloroindole-2-carbonyl chloride, via ethyl 4-[2-(5-chloroindole-2-carboxamido)-ethyl]-phenylacetate (m.p. 193°–195° C.), 4-[2-(5-chloroindole-2-carboxamido)-ethyl]-phenylacetic acid; m.p. 242°–243° C., after recrystalization from ethanol/toluene;

(d) with 5-chloro-2-methylbenzo[b]furoyl chloride, via ethyl 4-[2-(5-chloro-2-methylbenzo[b]furoyl-(7)-amino)- ethyl]-phenylacetate (oil), 4-[2-(5-chloro-2-methylbenzo[b]furoyl-(7)-amino)-ethyl]- phenylacetic acid; m.p. 166°–168° C., after reprecipitation.

EXAMPLE 18

In a manner analogous to that described in Example 11, by the reaction of ethyl 2-[4-(2-aminoethyl)-phenyl]-propionate hydrochloride with 5-chloro-2-(2-methoxyethoxy)-benzoyl chloride (m.p. 49°–51° C.), there is obtained, via ethyl 2-{4-[2-(5-chloro-2-(2-methoxyethoxy)-benzamido)-ethyl]-phenyl}-propionate (oil), 2-{4-[2-(5-chloro-2-(2-methoxyethoxy)-benzamido)-ethyl]-phenyl}-propionic acid; m.p. 94°–96° C., after recrystallization from isopropanol/water.

EXAMPLE 19

In a manner analogous to that described in Example 11, there are obtained, by reaction of ethyl 2-[4-(2-aminoethyl)-phenyl]-butyrate hydrochloride (a) with 5-chloropentyloxybenzoyl chloride (b.p. 147°–148° C./0.5 mm Hg), via ethyl 2-{4-[2-(5-chloro-2-pentyloxybenzamido)-ethyl]-phenyl}-butyrate (oil), 2-{4-[2-(5-chloro-2-pentyloxybenzamido)-ethyl]-phenyl}-butyric acid; m.p. 124°–126° C., after recrystallization from 80% isopropanol;

(b) with 5-trifluoromethyl-2-methoxybenzoyl chloride, via ethyl 2-{4-[2-(5-trifluoromethyl-2-methoxybenzamido)-ethyl]-phenyl}-butyrate, 2-{4-[2-(5-trifluoromethyl-2-methoxybenzamido)-ethyl]-phenyl}-butyric acid; m.p. 133°–136° C., after recrystallization from ethyl acetate.

For the preparation of ethyl 2-[4-(2-aminoethyl)-phenyl]-butyrate hydrochloride, ethyl 2-phenylbutyrate is chloromethylated and the ethyl 2-(p-chloromethylphenyl)-butyrate obtained (b.p. 117°–123° C./0.2 mm Hg) is reacted with potassium cyanide in acetone to give ethyl 2-(p-cyanomethylphenyl)-butyrate (b.p. 156°–160° C./0.3 mm Hg). By the catalytic hydrogenation of the nitrile group in the presence of a palladium/charcoal catalyst in alcoholic hydrochloric acid solution, there is obtained ethyl 2-[4-(2-aminoethyl)-phenyl]-butyrate hydrochloride, which does not crystallize.

EXAMPLE 20

2-{4-[2-(5-Chloro-2-methoxybenzamido)-ethyl]-phenyl}-butyric acid 6.2 g 2-[4-(2-Aminoethyl)-phenyl]-butyric acid hydrochloride are suspended in 100 ml acetone. After the addition of 50 ml 2 N aqueous sodium hydroxide solution, a solution of 4.8 g 5-chloro-2-methoxybenzoyl chloride in 50 ml acetone is added dropwise thereto at ambient temperature and the reaction mixture then stirred for 2 hours at 50° C. After cooling, the reaction mixture is evaporated in a vacuum and the aqueous solution acidified with dilute hydrochloric acid. The 2-{4-[2-(5-chloro-2-methoxybenzamido)-ethyl]-phenyl}-butyric acid obtained solidifies upon triturating with diisopropyl ether and is recrystallized from diisopropyl ether. The yield is 3.2 g (42.5% of theory); m.p. 120°–122° C.

The 2[4-(2-aminoethyl)-phenyl]-butyric acid hydrochloride used as starting material is prepared in the following manner: 2-phenylburyric acid is reacted with paraformaldehyde/hydrochloric acid to give 2-(4-chloromethylphenyl)-butyric acid (b.p. 173°–176° C./0.1 mm Hg). By the reaction thereof with potassium cyanide, there is obtained 2-(4-cyanomethylphenyl)-butyric acid (oil) which, after catalytic hydrogenation, gives 2-[4-(2-aminoethyl)-phenyl]-butyric acid hydrochloride; m.p. 128°–130° C.

EXAMPLE 21

(1-Phenethylbiguanide) 4-[2-(5-chloro-2-methoxybenzamido)-ethyl]-phenylacetate.

3.08 g sodium 4-[2-(5-chloro-2-methoxybenzamido)-ethyl]-phenylacetate (prepared from 4-[2-(5-chloro-2-methoxybenzamido)-ethyl]-phenylacetic acid and the equivalent amount of sodium methylate in methanol) and 2.0 g 1-phenethylbiguanide hydrochloride are heated under reflux in 100 ml absolute ethanol for 1 hour. Thereafter, the reaction mixture is evaporated to one half of its original volume, the precipitated sodium chloride is filtered off with suction and the filtrate is mixed with diethyl ether. The desired salt crystallizes out slowly and, for purification, is dissolved in ethanol and again precipitated out by the addition of diethyl ether. The salt thus obtained has a melting point of 121°–123° C.

EXAMPLE 22

In a manner analogous to that described in Example 11 by the reaction of ethyl 2-[4-(2-aminoethyl)-phenyl]-propionate hydrochloride with 3,5-dichloro-2-methoxybenzoylchloride, there is obtained, via ethyl 2-{4-[2-(3,5-dichloro-2-methoxy-benzamido)-ethyl]-phenyl}-propionate (oil), sodium 2-{4-[2-(3,5-dichloro-2-methoxybenzamido)-ethyl]-phenyl}-propionate; m.p. 238°–240° C.

The hypoglycaemic activity of the test compounds was tested in known manner as follows:

The test compounds were administered to male Sprague-Dawley rats with a body weight of 200–220 g by intraperitoneal injection (i.p.) as a solution of the sodium salt or per os (p.o.) as a Tylose suspension.

The test compounds were administered to rabbits either by intravenous injection (i.v.) into the ear edge vein as a solution of the sodium salt or per os through a stomach tube as a Tylose suspension.

In the following table, there is given the threshold dosage in mg/kg of body weight, i.e. the lowest dosage of compound required to produce a significant reduction in the blood sugar level, viz. about 15–20%.

For purposes of comparison, $N_1$-(sulfanilyl)-$N_2$-(n-butyl)-urea (sold under trade name "Nadisan") was tested under the same conditions.

The results are set forth in the following table:

Table

| Active material from example | Threshold dosage (mg/kg) | |
|---|---|---|
| | Rats | Rabbits |
| 1 | | 100 p.o. |
| 1 a | 100 p.o. | 50 p.o. |
| 1 b | | 100 p.o. |
| 2 | | 100 p.o. |
| 3 | | 100 p.o. |
| 3 a | 100 p.o. | 100 p.o. |
| 6 | 100 p.o. | 100 p.o. |
| 6 a | 50 i.p. | 11 35 i.v., 50 p.o. |
| 6 b | 50 p.o. | |
| 6 c | 25 i.p. (short) | 100 p.o. |
| 7 | 50 i.p. | 50 i.v. |
| 7 a | 50 i.p. | 25 i.v. |
| 7 c | 25 i.p. | 50 i.v. |
| 9 a | 25–50 i.p. | 100 p.o. |
| 9 b | <100 p.o. | 50 p.o. |
| 9 c | 25 i.p. | 50 p.o. |
| 9 d | | 100 p.o. |
| 9 e | | 100 p.o. |
| 11 | 25 i.p. (short) | 50 i.v. (short) |
| 12 | 100 i.p. | |
| 13 | 100 i.p. | |
| 13 a | 50 i.p. | 50 i.v. |
| 15 | 50 i.p. | 50 i.v. |
| 17 a | 50 i.p. | 100 i.v. |
| 17 b | 100 i.p. | 100 i.v. |
| 17 d | 35 i.p. | 25 i.v. |
| 18 | 25–50 i.p. | 50 i.v. (short) |
| 19 a | 10 i.p. | 25 i.v. |
| 22 | 50–100 i.p. | 100 i.v. |

Table-continued

| Active material from example | Threshold dosage (mg/kg) | |
|---|---|---|
| | Rats | Rabbits |
| Nadisan* | 25 i.p. | 200 i.v. |

*Nadisan = $N_1$ - (sulfanilyl) - $N_2$ - (n-butyl) - urea

The compounds (I) can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents (such as ethylene diaminetetraacetic acid), high molecular weight polymers (such as liquid polyethylene oxide) for viscosity regulation or polyoxyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

The material administered may be the acid or a salt or ester thereof. It is believed that due to hydrolysis in the body the active material is in all these instances the same, viz. probably the acid.

The novel compounds may be administered by themselves or in conjunction with carriers which are pharmacologically acceptable, either active or inert. The dosage units are similar to those of the heretofore known anti-cholesterol agents, e.g., about 0.2 to 2 grams per day for an adult or about 3–30 mg/kg per day although higher or lower dosages can be used. Rather than a single dose it is preferable if the compounds are administered in the course of a day, i.e., about four applications of 100 mg. each at spaced time intervals or 8 of about 50 mg. each. A convenient form of administration is in a gelatine capsule.

The dosage of the novel compounds of the present invention for the treatment of diabetes depends in the main on the age, weight, and condition of the patient being treated. The preferable form of administration is via the oral route in connection with which dosage units containing 50–500 mg. of active compound in combination with a suitable pharmaceutical diluent is employed. One or two unit dosages are good from one to four times a day.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

It will be appreciated that the instant specification and examples are set forth by way of illustration and not limitation, and that various modifications and changes may be made without departing from the spirit and scope of the present invention.

What is claimed is:

1. A phenylacetic acid derivative of the formula

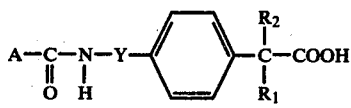

wherein
- A is an aryl radical substituted by halogen, trifluoromethyl, alkyl, alkoxy, alkenyloxy, alkoxyalkoxy, alkyl-substituted amino or aryloxy,
- Y is a valency bond or an optionally branched alkylene radical containing up to 3 carbon atoms, and
- $R_1$ and $R_2$ each independently is hydrogen or a lower alkyl radical, or a physiologically compatible salt or ester thereof.

2. A compound according to claim 1, wherein Y is an optionally branched alkylene radical containing up to three carbon atoms.

3. A compound according to claim 2 wherein A is a 2-alkoxy-5-halophenyl radical.

4. A compound according to claim 1 wherein such compound is 4-[2-(5-chloro-2-methoxybenzamido)-ethyl]-phenylacetic acid of the formula

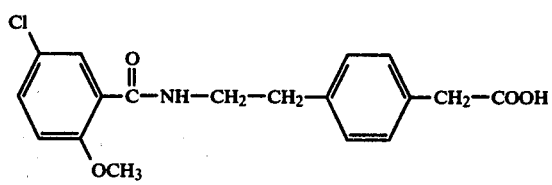

or a physiologically compatible salt or ester thereof.

5. A compound according to claim 1 wherein such compound is 4-[2-(5-bromo-2-methoxybenzamido)-ethyl]-phenylacetic acid of the formula

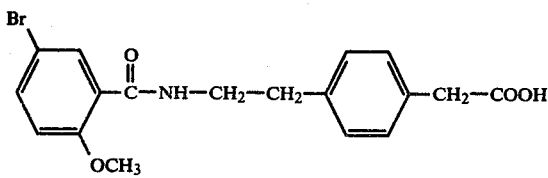

or a physiologically compatible salt or ester thereof.

6. A compound according to claim 1 wherein such compound is 2-{4-[2-(5-chloro-2-pentyloxybenzamido)-ethyl]-phenyl}-butyric acid of the formula

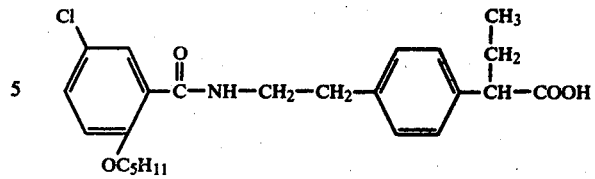

or a physiologically compatible salt or ester thereof.

7. A phenylacetic acid derivative of the formula

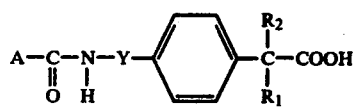

wherein
- A is an aryl radical optionally substituted by halogen, trifluoromethyl, alkyl, alkoxy, alkenyloxy, alkoxyalkoxy, alkyl-substituted amino or aryloxy,
- Y is an alkylene radical containing up to 3 carbon atoms,
- $R_1$ and $R_2$ each independently is hydrogen or a lower alkyl radical, or a physiologically compatible salt or ester thereof.

8. A compound according to claim 7,
wherein
- A is an aryl radical containing 6 to 10 carbon atoms optionally substituted by halogen; trifluoromethyl; or alkyl, alkoxy, alkenyloxy, alkoxyalkoxy, alkyl-substituted amino each with up to 4 carbon atoms or aryloxy containing 6 to 10 carbon atoms; and
- $R_1$ and $R_2$ each independently is a hydrogen atom or an alkyl radical with up to 5 carbon atoms.

9. A hypoglycaemically or hypolipidaemically active composition of matter comprising a hypoglycaemically or hypolipidaemically effective amount of a compound according to claim 1 or a physiologically compatible salt or ester thereof in admixture with a physiologically acceptable diluent.

10. A method of reducing the sugar or lipid level in the blood which comprises administering to a patient a hypoglycaemically or hypolipidaemically effective amount of a compound according to claim 1 or a phsiologically compatible salt or ester thereof.

11. The method according to claim 10, wherein said compound is
- 4-[2-(5-chloro-2-methoxybenzamido)-ethyl]-phenylacetic acid,
- 4-[2-(5-bromo-2-methoxybenzamido)-ethyl]-phenylacetic acid,
- 2-{4-[2-(5-chloro-2-pentyloxybenzamido)-ethyl]-phenyl}-butyric acid, or a physiologically compatible salt or ester thereof.

* * * * *